United States Patent [19]
Wickstrom

[11] Patent Number: 5,211,562
[45] Date of Patent: May 18, 1993

[54] METHOD AND APPARATUS FOR EVALUATING PHYSICAL ABILITY

[76] Inventor: Richard J. Wickstrom, 10911 Fernhill Dr., Cincinnati, Ohio 45241

[21] Appl. No.: 785,505

[22] Filed: Oct. 30, 1991

[51] Int. Cl.$^5$ ............................................. G09B 19/24
[52] U.S. Cl. .................... 434/260; 434/258; 434/259; 434/247
[58] Field of Search ........... 434/247, 258, 259, 260 X; 482/8.9; 73/379; 128/25 R, 26

[56] References Cited

U.S. PATENT DOCUMENTS

| | | |
|---|---|---|
| 1,664,210 | 3/1928 | Hall . |
| 2,985,451 | 5/1961 | Sims ........................................ 273/1 |
| 3,427,731 | 2/1969 | Debolt ................................... 35/13 |
| 3,488,053 | 1/1970 | Patel ....................................... 273/1 |
| 4,032,155 | 6/1977 | Thomas ............................... 273/156 |
| 4,377,050 | 6/1982 | Engalitcheff, Jr. ..................... 482/5 |
| 4,692,119 | 9/1987 | Ussery ................................... 434/259 |
| 4,768,783 | 9/1988 | Engalitcheff, Jr. ................. 482/139 |
| 4,773,398 | 9/1988 | Tatom .............................. 482/139 X |
| 4,795,351 | 1/1989 | Vermette ............................ 434/258 |
| 4,885,687 | 12/1989 | Carey .............................. 364/413.02 |
| 4,936,299 | 6/1990 | Glandson .......................... 128/25 R |

OTHER PUBLICATIONS

Brandon, et al., Manual for Valpar Component Work Sample 9, Whole Body Range of Motion, 1974, pp. 1-13a.
Brandon, et al., Manual for Valpar Component Work Sample 4 Upper Extremity Range of Motion, 1974, pp. 1-12, 19-20.
Valpar Int'l Corp., Manual for Dynamic Physical Capacities, VCWS 19, 1986, pp. 6-8, 27.
Crawford et al., Crawford Small Parts Dexterity Test 1981, pp. 3-4.
Tiffin, J., Purdue Pegboard Examiner Manual, 1968, pp. 2-5.
Bennett, G. K., Manual of Directions, Hand-Tool Dexterity Test, 1965, pp. 2-6.
Valpar Int'l Corp., VCWS 9, Whole Body Range of Motion, sales literature, 1986.
Valpar Int'l. Corp., VCWS 4, Upper Extremity Range of Motion, sales literature, 1986.
Valpar Int'l Corp. VCWS 19, Dynamic Physical Capacities, sales literature, 19.

*Primary Examiner*—John J. Wilson
*Assistant Examiner*—L. Thomas
*Attorney, Agent, or Firm*—Frost & Jacobs

[57] ABSTRACT

A method and apparatus is disclosed for the testing and evaluating of a person's dexterity, range of motion, and dynamic lifting ability. The dexterity testing includes methods which can evaluate the wrist and hand range of motion by requiring the person to move his wrist through the normal range of motions, including flexion, extension, pronation, and supination. The person undergoes the same test and evaluation at each of three working heights: (1) elbow height, (2) overhead height, and (3) knee height, providing a functional assessment of dexterity and range of motion of the person's entire musculoskeletal system. The lifting ability testing includes both an upper body lifting evaluation (to shoulder height) and a lower body lifting evaluation (to carry height). Each of the two evaluations is tested independently.

7 Claims, 9 Drawing Sheets

METHOD AND APPARATUS FOR EVALUATING PHYSICAL ABILITY

TECHNICAL FIELD

The present invention relates generally to physical ability testing methods and equipment, and is particularly directed to testing methods of the type which functionally assess a person's dexterity, range of motion, and dynamic lifting ability. The invention will be specifically disclosed in connection with a procedure that evaluates a person's lifting ability at different work levels, and tolerances for working with awkward grip/wrist postures while working with the arms elevated (overhead height), mid-range (elbow height), and below waist (knee height).

BACKGROUND OF THE INVENTION

For years, medical and vocational evaluators have been testing and otherwise attempting to evaluate dexterity and other physical qualifications of applicants and workers to assist in safe and productive placement in specific jobs. Most of these tests measure one or more of the physical demands and aptitudes of jobs which are specified in the Dictionary of Occupational Titles. Examples of tests which evaluate dexterity of arms, wrists, and hands are the Purdue Pegboard Test by Science Research Associates, Inc., the Hand-Tool Dexterity Test by The Psychological Corporation, the Crawford Small Parts Dexterity Test by The Psychological Corporation, and the Valpar Corporation Component Work Sample 4 test. A further test of this nature is disclosed in U.S. Pat. No. 4,795,351.

The Purdue Pegboard Test evaluates dexterity for two types of activities, (1) gross movement of hands, fingers, and arms, and (2) "fingertip" dexterity. The person being tested is seated at a table while undergoing the test, and the test apparatus rests on that table. The person must pick up pins, washers, and collars while using either his dominant hand, or his "other" hand. The pins, washers, and collars are rather small in size, so the person must use his "fingertip" dexterity in manipulating those parts.

The Hand-Tool Dexterity Test evaluates a person's proficiency in using ordinary mechanics' tools. This test is specifically designed to minimize the advantage gained by superior planning ability, but instead, tests the combination of aptitude and achievement based on past experiences in tool use. The test apparatus rests on a work bench or table which is 34 inches above the floor. The test subject must loosen nuts on bolts by use of wrenches, and then after some loosening, by use of his fingers.

The Crawford Small Parts Dexterity Test evaluates fine eye-hand coordination. The person being tested is seated at a table while undergoing the test, and the test apparatus rests on that table. The test subject must use tweezers to insert small pins in close-fitting holes in a plate and then place small collars over the protruding pins. The test subject must also start small screws in threaded holes in a plate and then use a screwdriver to screw them down.

The Valpar Component Work Sample 4 test (VCWS 4) evaluates the upper extremity range of motion, including the shoulder, upper arm, forearm, elbow, wrist, and hand. This test gives an evaluator an actuarial level of a person's neck and back fatigue, finger dexterity and finger tactile sense. These factors are not measured independently, but as they relate to an entire range of motion in a work stress situation. The normal test has the person standing in front of a work table or work bench, however the test can be used with a disabled person who is sitting. The test apparatus consists of a five-sided square box which has each of its sides lined with visually obscured bolts which have threads protruding into the interior of the square box. The front side of the square box has a circular opening so that a person's hand can be inserted inside the box. A second portion of the apparatus consists of a nut tray which is placed on the right or left side of the box, depending upon which hand is the dominant hand of the test subject. To perform the test, the test subject must pick up one nut at a time from the nut tray and place it on each of the bolts inside of the box. After each of the sides of the box has had nuts threaded onto each of the bolts, the test subject then disassembles those nuts from each of the bolts. Each hand is tested separately. The entire test is timed, and the test duration for the average person is around 27 minutes. VCWS 4 does not teach nor suggest the use of its box apparatus at different elevations when used with a test subject.

The test disclosed in U.S. Pat. No. 4,795,351, to Vermette also consists of a five-sided box which has bolts lining each of the box sides which have threads facing the interior of the box, and also has a circular opening in one of the sides of the boxes for placing the human hand into the interior of the box. In addition, Vermette includes interior partitions to make it more difficult to get at the bolts which are protruding through the exterior surfaces of the box, and to get at the nuts which are on the bolts. Vermette includes a test method which is designed to simulate manual operations by use of an enclosed, partitioned box, which is visually obscured. Vermette does not teach nor suggest the use of its box apparatus at different elevations when used with a test subject.

All of the above tests consist of procedures that are to be performed at table-top height, and not at elevations above the test subject's head or below the test subject's knees. It is, therefore, obvious that each of the above tests evaluates a person's dexterity level at an elevation which is the easiest for a human to perform at, and does not evaluate the dexterity of a person's arms or wrists at elevations which are more difficult to work at.

Valpar Corporation offers two other testing methods and apparatus for evaluating other aspects of a person's dexterity. The Valpar Component Work Sample 9 (VCWS 9) evaluates a whole body range of motion. VCWS 9 is specifically designed to test a person's dexterity while that person repeatedly moves from one position to another, while doing certain tasks, generally transferring items from one height location to another height location. VCWS 9 is specifically designed to be different from other commonly used tests, wherein the person is either sitting or standing comfortably. The person being evaluated must remove a number of nuts from bolts which are permanently attached to the test fixture, and then place those nuts into a nut tray, which is at about chest level. After all the nuts are removed from a particular location, a plastic form, such as a square or a triangle is then removed from the bolts and then placed upon a similar pattern of bolts which is at a different elevation. At that point, the test subject removes nuts from the nut tray and screws them down over bolts, thus holding the plastic form in place at that elevation. The test procedure starts at forms which are at eye level, then proceeds to an overhead level, then to waist level, then to knee level, and, finally, back to eye level. The overall test requires around 30 minutes for the average person to complete. While performing the overhead portion of the test, the test subject must repeatedly reach down to grab a nut from the nut tray, and then reach back up to the overhead level for placement of that nut. For the portion of the test that takes place at the knee level, the person must repeatedly reach up to grab a nut from the nut tray, and then stoop in order to place the nut at the proper bolt. VCWS 9 thus achieves its purpose of forcing the test subject to repeatedly move around, rather than maintaining fixed posture during each part of the test.

The Valpar Component Work Sample 19 (VCWS 19) evaluates a person's dynamic physical capacities. The purpose of this test is to give an objective measure of the Physical Demands Factor of the Worker Qualifications Profile of the *Dictionary of Occupational Titles*. VCWS 19 evaluates the five different strength levels of the physical demands factors: 10, 20, 50, 100, and over 100 pounds. VCWS 19 also allows observation of certain subfactors such as: climbing and balancing, stooping, crouching, reaching handling, standing, walking, carrying, lifting, fingering (feeling), pushing and pulling, kneeling, talking and hearing, and seeing. VCWS 19 is very dynamic in nature, and differs from most physical tolerance exercises which require a person to work in a more stationary position. The test additionally evaluates endurance along with strength; once the person's strength level has been established, he continues to work at that level for about 20 minutes. The test procedure is as follows: (1) a test subject reads an invoice, (2) locates a shipping carton, (3) removes a shipping carton from a shelf, sometimes having to climb up on a ladder, (4) packs the carton properly, and (5) weighs the carton and places it in the proper place for shipping. In carrying out this exercise, the test subject performs tasks which are very similar to those of a shipping and receiving clerk, or a parts order clerk.

The Valpar VCWS 9 whole body range of motion tester and the Valpar VCWS 19 dynamic physical capacities tester evaluate a person's dexterity and physical capacity, respectively, while moving through a wide range of motions. However, neither Valpar test is designed to determine whether a specific work height or posture causes a particular problem for the test subject. In other words, if a particular work posture or work height causes a particular problem for the test subject, both Valpar VCWS 9 and VCWS 19 tests can only determine that a particular set of motions has slowed the test subject down. Neither of these Valpar tests can identify which single particular position was the cause of the test subject's problem.

Health care professionals such as physicians have not widely used objective tests of physical abilities to make placement decisions, because of the time and expense of such vocational testing. The above mentioned Valpar VCWS 9 and VCWS 19 testing equipment both take up a large amount of space within a given room of a building. In addition, each of these two tests takes a relatively long period of time for a test subject to perform, thus making it difficult to test a large number of persons in medical or employee health settings. Vocational evaluators who use such time consuming work samples are not able to respond cost effectively to the needs of competitive industry.

SUMMARY OF THE INVENTION

Accordingly, it is a primary object of the present invention to provide a portable testing apparatus which can be used to test physical abilities within a small area of space.

It is another object of the present invention to provide a portable testing apparatus which can be used to objectively evaluate dexterity at different work levels, such as above the head with the arms elevated, elbow height (midrange level), and below waist level while the person is crouching or kneeling. At each work level, the test subject must perform a dexterity activity while enduring awkward grip and wrist postures.

It is a further object of the present invention to provide a portable testing apparatus which can be used to objectively evaluate lifting ability at different levels which can be adjusted for the height of each test subject. In this way, the testing apparatus can be adapted in order to fairly test each subject at various levels that correspond to his particular anthropometry, rather than testing him against a set of shelves which are fixed at a standard height, and which the test subject may use a ladder or steps to properly work with those shelves. The present invention thus provides a streamlined test which evaluates the important physical work factors without the requirement of additional equipment.

It is a yet further object of the present invention to provide a portable testing apparatus in which vision is not obscured, which then allows for the testing of females on a more equal basis as compared to men.

It is still another object of the present invention to provide a method of evaluating a human test subject's dexterity and lifting ability while working at various heights, by use of a single, portable test apparatus which occupies little physical area.

It is yet another object of the present invention to provide a method of evaluating a human test subject's dexterity and lifting ability at various heights within a relatively short period of time, so that many such test subjects can be quickly processed by use of a single test apparatus.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved method is provided for testing and evaluating the dexterity and range of motion of a person. The test subject performs disassembly and reassembly of a number of nuts and bolts while subjecting his wrists to the normal range of motions including flexion (bending forward), extension (bending backward), pronation (where the back of the hand faces the test subject's eyes), and supination (where the palm of the hand faces the test subject's eyes). The disassembly and reassembly procedure is performed at three levels, (1) elbow height, (2) overhead height, and (3) below waist (knee) height. Each level is independently adjustable so that the test subject's physical size is correctly accounted for in evaluating his dexterity at prescribed levels which are related to his physique, rather than being related to some standard shelf height.

In accordance with another aspect of the invention, a method is provided for testing and evaluating the dexterity and range of motion of a person's upper extremities and neck at both elbow height and at overhead height while the person is seated in a wheelchair. The test subject performs disassembly and reassembly of a number of nuts and bolts while subjecting his wrists to the normal range of motions including flexion, extension, pronation, and supination. The disassembly and reassembly procedure is performed at only two levels, elbow and overhead height. The levels are independently adjustable so that the test subject's physical size is correctly accounted for in evaluating his dexterity at each prescribed level which is related to his physique and wheelchair size, rather than being related to some standard shelf height.

In accordance with a further aspect of the invention, an improved method is provided for testing and evaluating the ability of a person to lift known weights to various shelf levels. The test subject performs lower body lifting from floor height, pivoting, carrying to a lower shelf level, and upper body lifting (to an upper shelf level) using ever increasing weights until his upper and lower body lifting abilities have been determined. The two shelf levels are independently adjustable so that the test subject's physical size is correctly accounted for in evaluating his lifting ability at prescribed levels which are related to his physique, rather than being related to some standard shelf height.

In accordance with a still further aspect of the invention, a method is provided for testing and evaluating the ability of a person who is experiencing lower back pain to lift known weights to various shelf levels. The test subject performs lower body lifting while positioning his back in an erect position, pivoting, walking while carrying the weight (to a lower shelf level), and upper body lifting (to an upper shelf level) using ever increasing weights until his lower and upper body lifting ability have been determined. The two shelf levels are independently adjustable so that the test subject's physical size is correctly accounted for in evaluating his lifting ability at prescribed levels which are related to his physique, rather than being related to some standard shelf height.

According to another aspect of the invention, an improved apparatus is provided for testing and evaluating the dexterity and range of motion of a person. The apparatus can be configured as a portable test fixture, having rollers mounted to the bottom of the test fixture for ease of movement, or as a wall-mounted test fixture that is permanently attached to a wall. In either configuration, the test fixture includes a vertical support which contains position holes at two-inch intervals, so that horizontal shelves may be attached to the vertical support at various heights. The test fixture includes two horizontal shelves at the lower and upper positions along the vertical support, and a horizontal mounting bracket with attached mounting plate at the overhead position along the vertical support. A dexterity testing apparatus is included which contains a large number of nuts and bolts for disassembly and reassembly while a person is subjecting his wrists to the normal range of motions including flexion, pronation, and supination. The dexterity testing apparatus can be positioned in three locations, at the lower and upper shelves and at the overhead mounting plate. Each shelf or bracket position is independently adjustable so that the test subject's physical size is correctly accounted for in evaluating his dexterity at prescribed levels (elbow height, overhead height, and knee height) which are related to his physique, rather than being related to some standard shelf height.

According to a further aspect of the invention, the improved apparatus for testing and evaluating the dexterity and range of motion of a person's upper extremities and neck also can be used in testing a handicapped person who is sitting, for example, in a wheelchair. The portable test fixture has a floor support which is wide enough to permit a standard-sized wheelchair to be positioned just in front of the shelves of the test fixture. In the first test of this instance, the upper shelf is raised up (out of the way) and only the lower shelf is used along with the dexterity testing apparatus. This shelf is adjustable in height so that the test subject's physical size is correctly accounted for in evaluating his dexterity at the seated level, which is related to the position he would normally work in, rather than being related to some standard shelf height. A second test can also be performed, wherein both shelves are raised out of the way, and the dexterity testing apparatus is attached to the overhead mounting bracket. This overhead mounting bracket is adjustable in height so that the test subject's physical size is correctly accounted for in evaluating his dexterity and range of motion at the overhead level, which is related to his physique, rather than being related to some standard shelf height.

According to a yet further aspect of the invention, the dexterity testing apparatus can be turned upside-down and placed upon a flat surface, such as a table or a work bench, and used as an independent tool for testing the dexterity of a person's upper extremities. In some ways, this use of the dexterity testing apparatus would be very similar to the instance wherein a test subject is seated in front of the portable test fixture that included a upper shelf (at elbow height) with a dexterity testing apparatus attached.

According to a still further aspect of the invention, the majority of the dexterity testing apparatus is made of a clear material so that the test subject's vision is not obscured when he is attempting to disassemble or reassemble nuts and bolts that are on the far side of the center divider of the dexterity testing apparatus. This aspect of the invention provides a dexterity test of a person's upper extremities which is more fair to women, and allows women to have more-equal scores to those of men.

According to yet another aspect of the invention, an improved apparatus is provided for testing and evaluating the ability of a person for lifting known weights to various shelf levels. The apparatus can be configured as a portable test fixture, having rollers mounted to the bottom of the test fixture for ease of movement, or as a wall-mounted test fixture that is permanently attached to a wall. In either configuration, the test fixture includes a vertical support which contains position holes at two-inch intervals, so that horizontal shelves may be attached to the vertical support at various heights. The test fixture includes two horizontal shelves at the lower and upper positions along the vertical support, and a horizontal mounting bracket with attached mounting plate at the overhead position along the vertical support. An industrial tote pan with handles is included for containing bags of leadshot of various weights and which can be used in the testing a person's lifting ability wherein bags of leadshot are incrementally added (in five or ten pound increments) to the weight already in the tote pan as the test subject performs the test. The tote pan can be placed onto shelves of the apparatus in two locations, at the lower and upper shelves. Each shelf position is independently adjustable so that the test subject's physical size is correctly accounted for in evaluating his upper body and lower body lifting abilities at prescribed levels (elbow height and knee height) which are related to his physique, rather than being related to some standard shelf height.

According to still another aspect of the invention, the improved apparatus for testing and evaluating the lifting ability of a test subject can also be used with a person who is experiencing lower back pain. The apparatus can be configured as either a portable test fixture or as a wall-mounted test fixture. In either configuration, the test fixture includes two horizontal shelves at the lower and upper positions along the vertical support. An industrial tote pan with handles is included for containing bags of leadshot of various weights and which can be used in the testing a person's lifting ability wherein bags of leadshot are incrementally added (in five or ten pound increments) to the weight already in the tote pan as the test subject performs the test. The tote pan can be placed onto shelves of the apparatus in two locations, at the lower and upper shelves. Each shelf position is independently adjustable so that the test subject's physical size is correctly accounted for in evaluating his upper body and lower body lifting abilities at prescribed levels (elbow height and knee height) which are related to his physique, rather than being related to some standard shelf height. In this instance, however, the tote pan does not rest on the floor at the start of each portion of the test, but instead rests upon a portable cart which has a hydraulic lift to bring the level of the tote pan high enough so that the test subject may pick up the tote pan while standing in an erect position. In this manner, the test subject may complete the lifting ability test without aggravating his lower back pain.

Still other objects of the present invention will become apparent to those skilled in this art from the following description wherein there is shown and described a preferred embodiment of this invention, simply by way of illustration, of one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE PREFERRED EMBODIMENT

Reference will now be made in detail to the present preferred embodiment of the invention, an example of which is illustrated in the accompanying drawings, wherein numerals indicate the same elements throughout the views.

Figure 1:
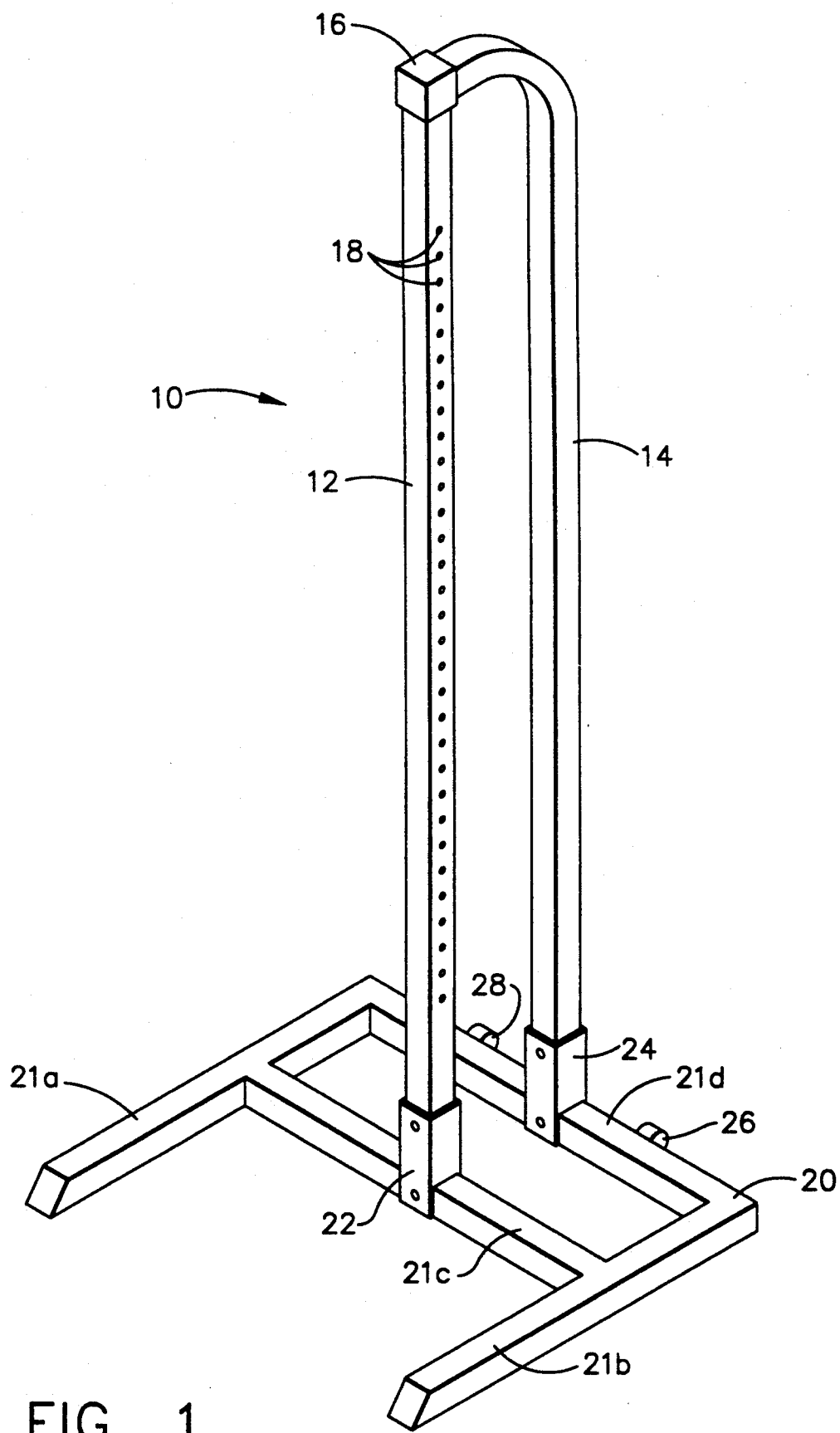
FIG. 1 is a perspective view of the support frame of a portable testing apparatus constructed in accordance with the present invention.

Referring now to the drawings, FIG. 1 shows the support frame of the testing apparatus of the present invention, nominally designated by the numeral 10. The frame consists of two vertical supports, a front vertical support 12 and a rear vertical support 14. The front vertical support 12 is constructed of hollow steel channel, and has a plurality of equally spaced position holes 18 along its sides, the holes 18 being spaced at two inch intervals. In the illustrated embodiment, front vertical support 12 is seven feet long.

The rear vertical support 14 also is made of hollow steel channel, and has a bend in its top position so as to join the front vertical support 12 at a top coupling 16. The top coupling 16 is made of steel channel and has a locking bolt and nut arrangement (not shown) so as to keep the supports 12 and 14 in position.

The base of the frame 10 consists of the floor support generally designated with the numeral 20 and defined by a pair of spaced channel legs 21a, and 21b. These channel legs 21a and 21b are joined by a pair of cross channels 21c and 21d, arranged in perpendicular relationship to the channel legs 21a and 21b. The channel legs 21a and 21b are separated by a distance that is sufficient for a standard wheelchair to be rolled up to the cross channel 216 without interfering with the floor support 20. Floor support 20 is constructed of hollow steel channel, and has two rollers 26 and 28 rotatably attached to the cross channel 21d on the rear portion of the floor support 20. The rollers 26 and 28 make it possible to slightly tilt the entire testing apparatus frame 10 backward, and then roll it along the floor. The front and rear vertical supports 12 and 14 are attached to the cross channels 21c and 21d respectively by use of the front lower coupling 22 and the rear lower coupling 24. The couplings 22 and 24 are preferably formed of hollow cold rolled steel channel.

If portability is not required in a given installation of the testing apparatus, then the front vertical support 12 can be bolted directly to a vertical wall. The other portions of the testing apparatus support frame 10 are not required in such an installation.

Figure 2:
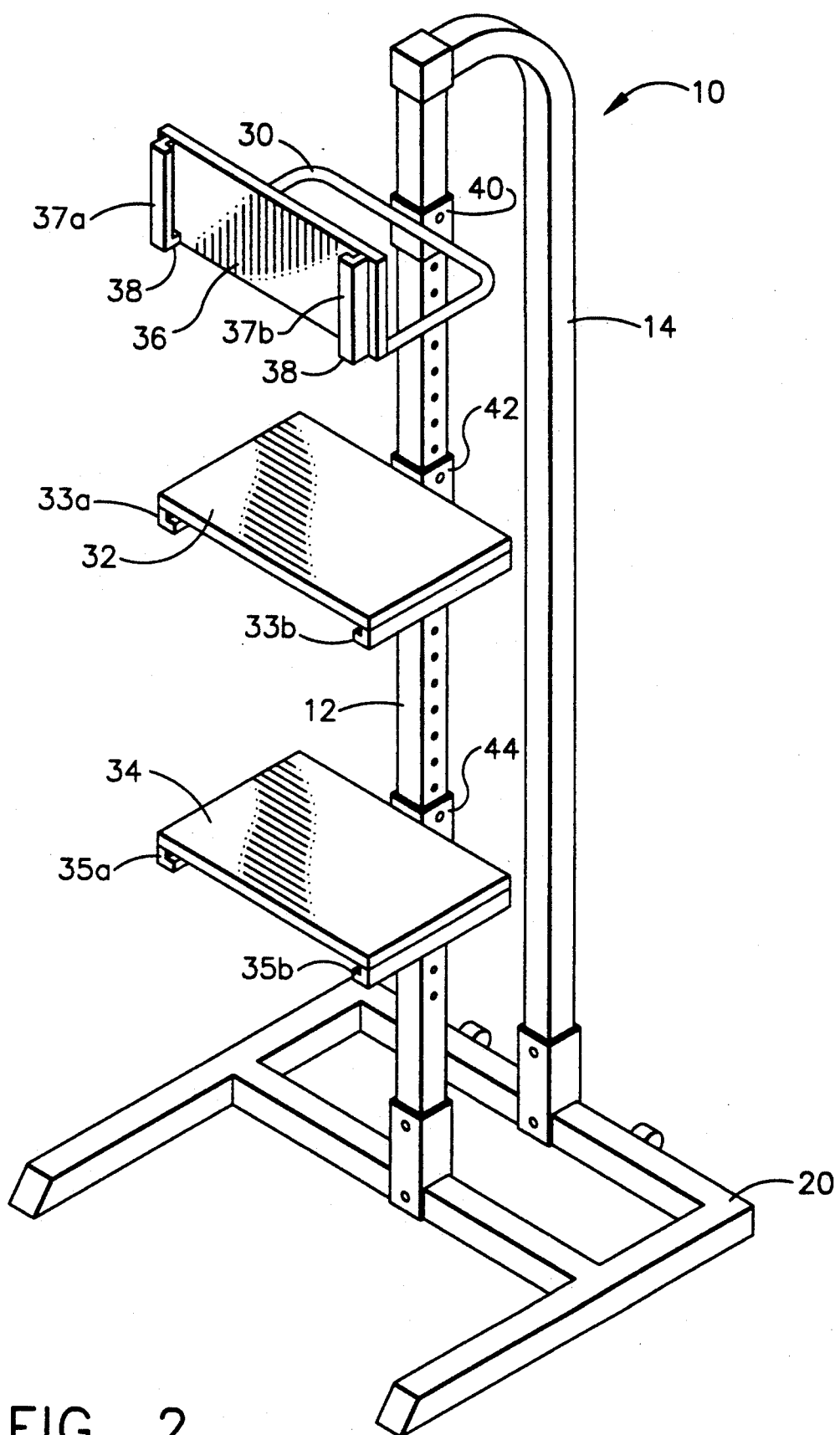
FIG. 2 is a perspective view of the portable testing apparatus of FIG. 1 with two shelves and an overhead horizontal mounting bracket.

As depicted in FIG. 2, the testing apparatus includes two shelves 32 and 34 and a horizontal mounting bracket 30, which shelves and brackets are attached to the front vertical support 12 by respective locator pin assemblies 40, 42, and 44. The overhead horizontal mounting bracket 30 is made of cold rolled steel rod in the illustrated embodiment, and has an overhead mounting plate 36 attached to its front-most locations. Overhead mounting plate 36 is composed of a vertical, thin steel plate, and has two mounting brackets 37a and 37b running vertically along the face of overhead mounting plate 36. A stop 38 is affixed near the bottom of each of the vertically running mounting brackets 37a and 37b, for preventing the dexterity testing apparatus 50 (see FIG. 4), once installed, from sliding put of the mounting brackets 37a and 37b of overhead mounting plate 36. The rear portion of overhead horizontal mounting bracket 30 is attached to a movable overhead shelf locator pin assembly 40. The shelf locator assembly 40 can slide up and down the front vertical support 12. Overhead shelf locator pin assembly 40 has holes in its sides so that the locator pin portion (not shown) of assembly 40 can protrude through those holes, and also through a pair of position holes 18 which are formed in the front vertical support 12. In this way, the overhead horizontal mounting bracket 30 can be located at any of the two-inch positions along the front vertical support 12.

Upper shelf 32 is formed of 12 gauge cold rolled steel in the illustrated embodiment, and is attached to the upper shelf locator pin assembly 42 at its rear. Upper shelf 32 has two mounting brackets 33a and 33b running horizontally along the lower surface of upper shelf 32. The lower shelf 34 is constructed similarly to upper shelf 32, and is attached at its rear to lower shelf locator pin assembly 44, and has mounting brackets 35a and 35b. Both pin assemblies 42 and 44 are constructed in a similar fashion to the overhead bracket locator pin assembly 40, and operate in the same manner with the use of locator pins. By use of this construction, the upper shelf 32 and the lower shelf 34 can be mounted at any of the two-inch position holes in the front vertical support 12.

Figure 6:
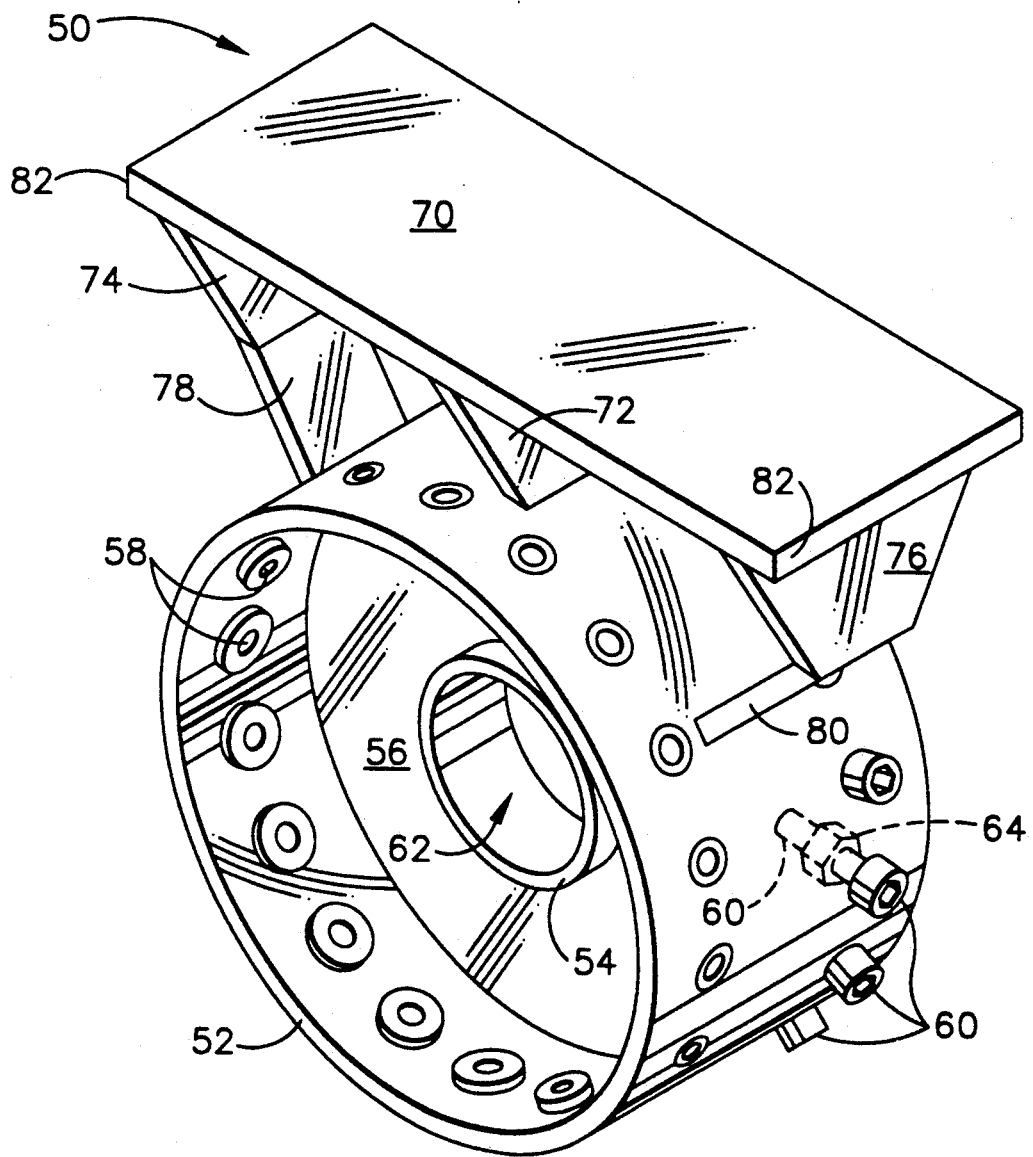
FIG. 6 is a detailed perspective view of the dexterity testing apparatus illustrated in FIGS. 2-5.

The dexterity testing apparatus 50 is depicted in FIG. 6. Dexterity testing apparatus 50 consists of an outer ring 52, a planar divider 56 which is perpendicular to the outer ring 52, and a removable center hub 54 which is concentric to outer ring 52 and is attached to the inner portions of the divider 56. In the illustrated embodiment, outer ring 52 and divider 56 are constructed of clear acrylic plastic. The removable center hub 54 is constructed of UHMW (ultra-high molecular weight) polyethylene in the illustrated embodiment, and is not necessarily transparent. The outer ring 52 has a series of radial holes 58 which are large enough in diameter to allow bolts 60 to pass through the holes. The radial holes 58 have smooth inner diameters so as to allow bolt 60 to cleanly pass through without having to be threaded. Holding bolts 60 in place are mating nuts 64. In the illustrated embodiment, there are eighteen radial holes 58 on each side of the divider 56, for a total of 36 radial holes 58. One-half of holes 58 are fitted with the nuts and bolts 60 and 64, for a total of eighteen bolts 60 and eighteen nuts 64, all located on one side of the divider 56.

Figure 7:
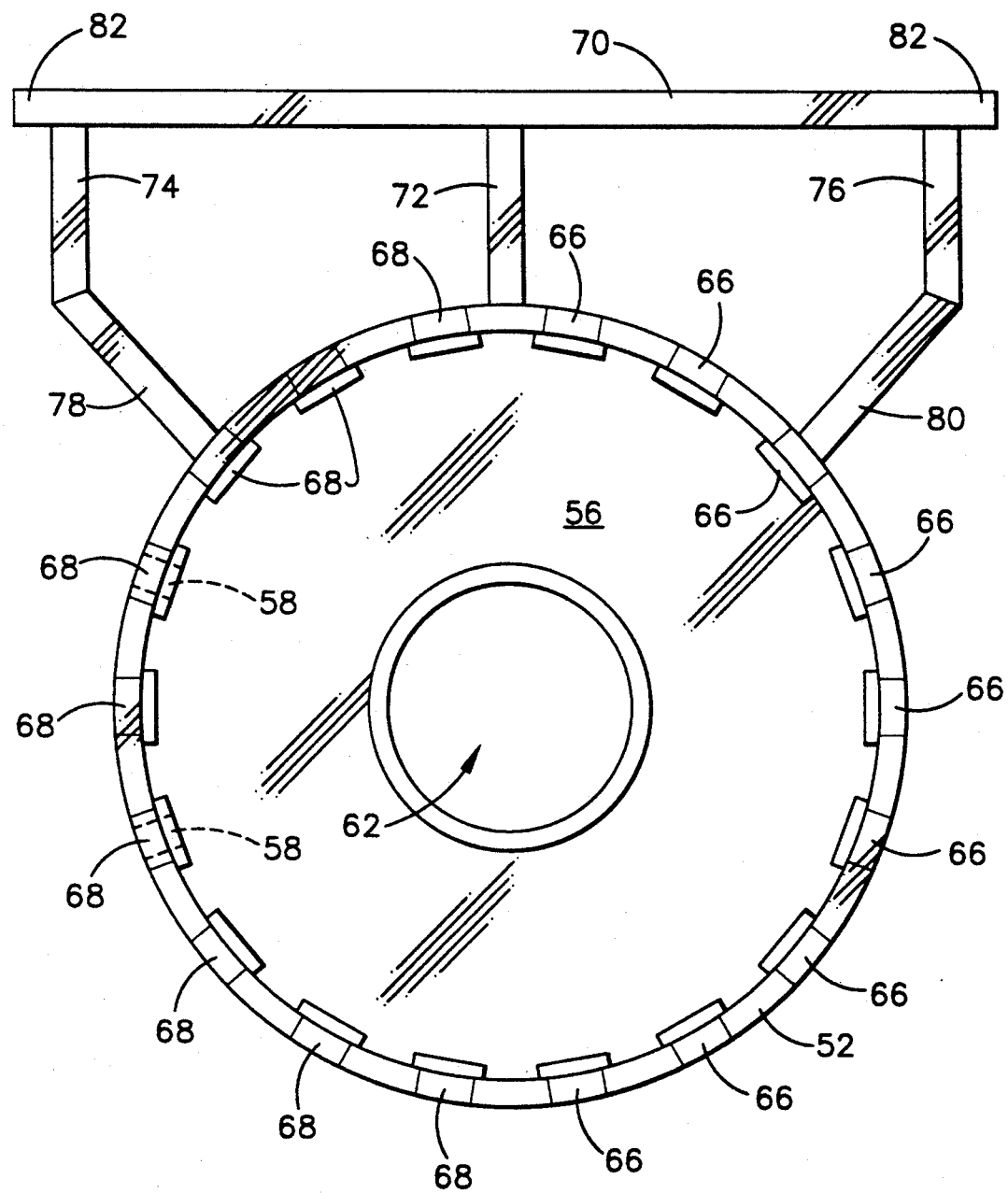
FIG. 7 is a front elevational view of the dexterity testing apparatus of FIG. 6.
Figure 8:
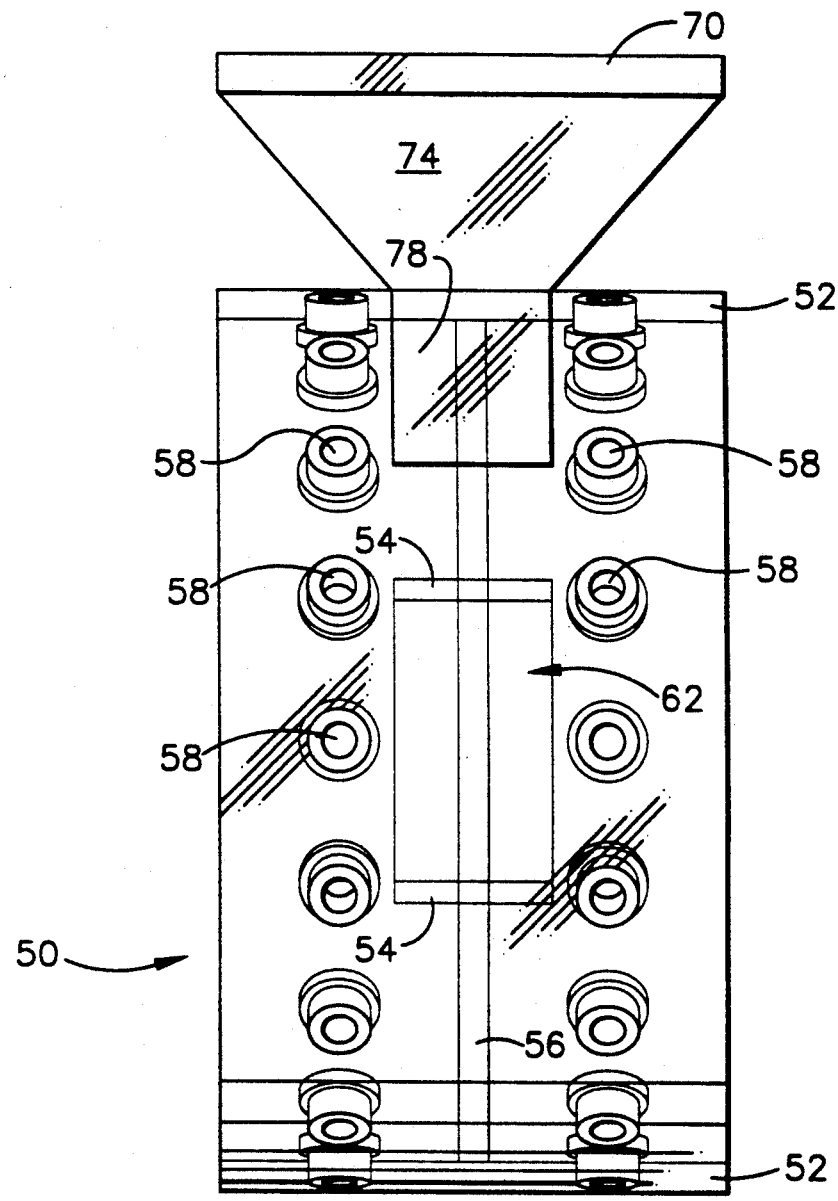
FIG. 8 is a side elevational view of the dexterity testing apparatus of FIG. 6.

As seen from the depiction of FIG. 7, the radial holes 58 have cylindrical inserts 66 and 68. The inserts 66 are coded with a first color, such as white, and the inserts 68 are coded with a different color, such as black. The white inserts 66 are located in the nine holes in the side of the dexterity testing apparatus 50 to the right of FIG. 7 with the black inserts 68 being located in the nine holes to the left side of the apparatus 50 in the same drawing. The white inserts 66 show the location of the specific nuts 64 and bolts 60 which are to be handled when the test subject's left hand is protruding through the hollow opening 62, while the black inserts 68 show the location of the specific nuts 64 and bolts 60 to be handled by the test subject's right hand while protruding through the hollow opening 62. Both of inserts 66 and 68 are cylindrical in shape, having a hollow opening through their centers, and are pressed into position (like bushings) within each of the eighteen radial holes 58. Each insert 66 or 68 also has a washer-like portion, which acts as a positioning flange on the inner side of the outer ring (see FIG. 7). The inserts 66 and 68 are preferably made of plastic.

The removable center hub 54 is hollow at its center-most portion, which center-most portion is designated by the numeral 62. The inner diameter of the hollow opening 62 is large enough to allow the human hand and wrist to fit through the opening. The function of the hollow opening 62 is to allow a person's hand through the opening while keeping his forearm substantially parallel to the centerline of the opening, thus forcing him to place his wrist in relatively awkward postures in order to perform the dexterity testing. On the other hand, if a person cannot place his wrist in the normal awkward positions that are required in order to perform the dexterity testing, then the entire center hub can be removed so that he may keep his wrist in a more straight posture while performing the dexterity testing. This, of course, would not be a test that could be compared to other persons' timing scores which are based on the normal awkward wrist positions.

The dexterity testing apparatus 50 also includes a planar mounting plate 70, which has three perpendicular supports 72, 74, and 76. The center perpendicular support 72 is attached between the planar mounting plate 70 and the outer ring 52. The left perpendicular support 74 and the right perpendicular support 76 are respectively attached to a left mounting bracket 78 and a right mounting bracket 80. Mounting brackets 78 and 80 are, in turn, mounted directly to the outer ring 52. Planar mounting plate 70 includes two outwardly extending protrusions 82 in the illustrated embodiment.

Figure 3:
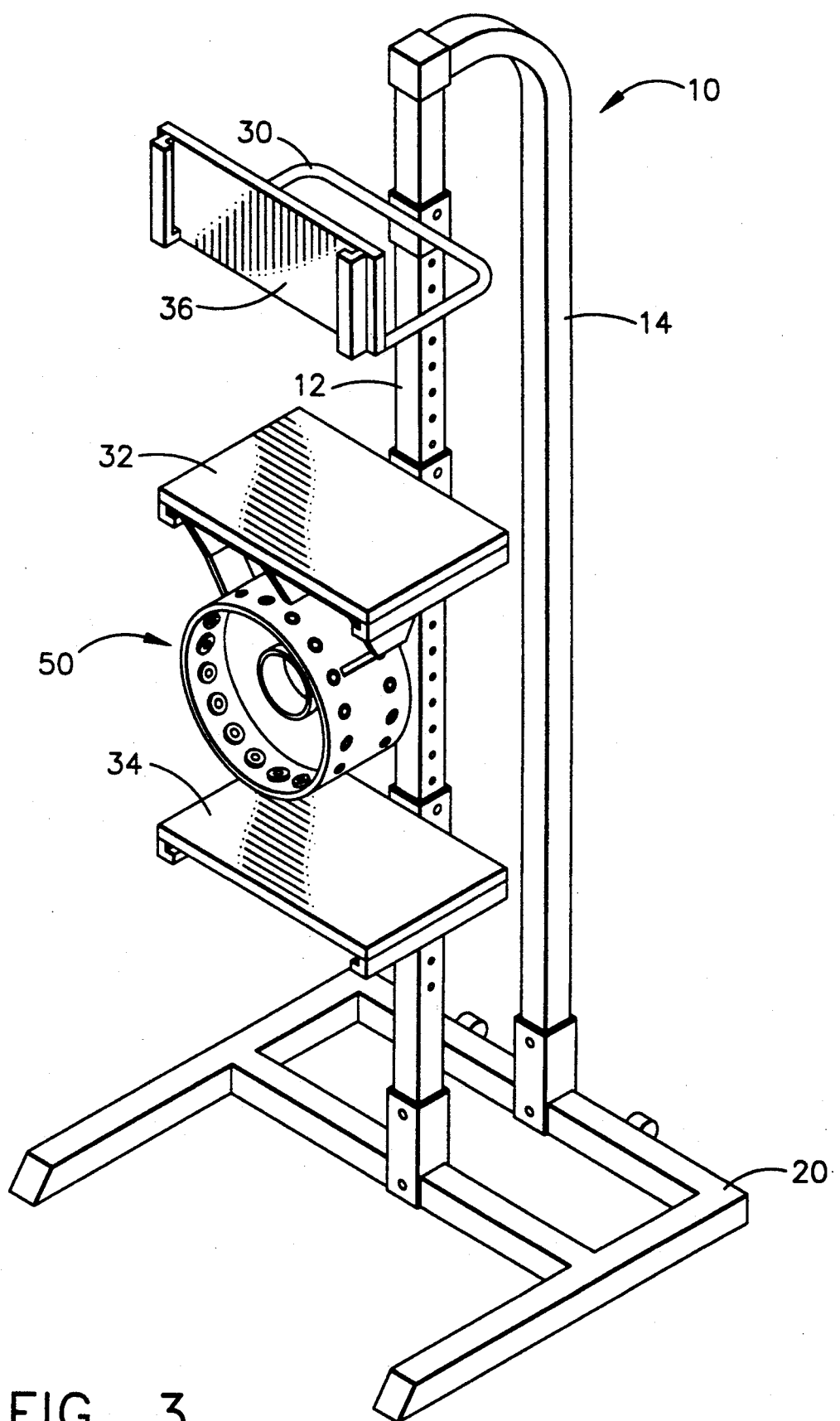
FIG. 3 is a perspective view of the portable testing apparatus shown in FIG. 2 with a dexterity testing apparatus attached at an elbow height position.
Figure 4:
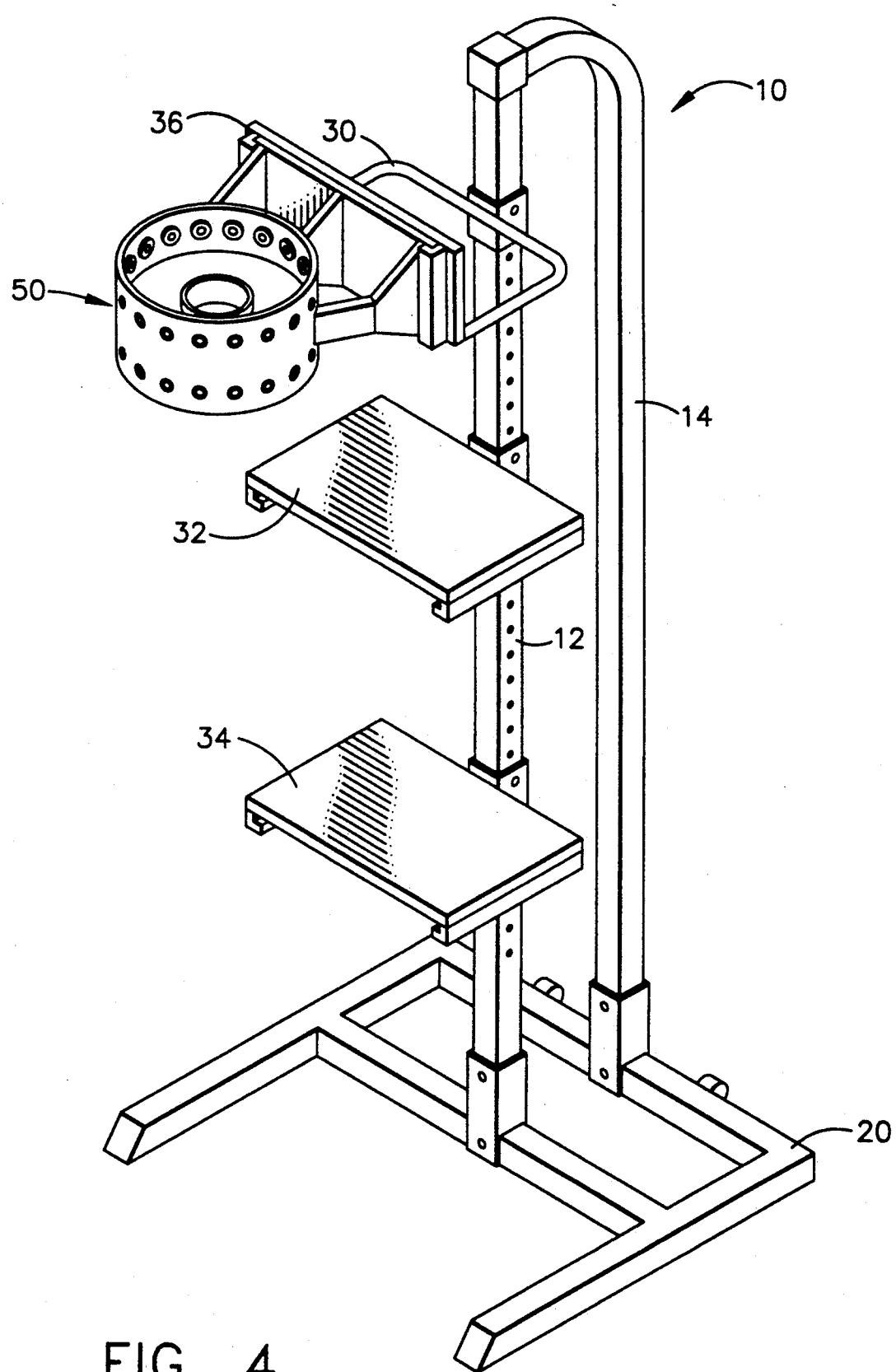
FIG. 4 is a perspective view of the portable testing apparatus of FIG. 2 with the dexterity testing apparatus attached at an overhead position.
Figure 5:
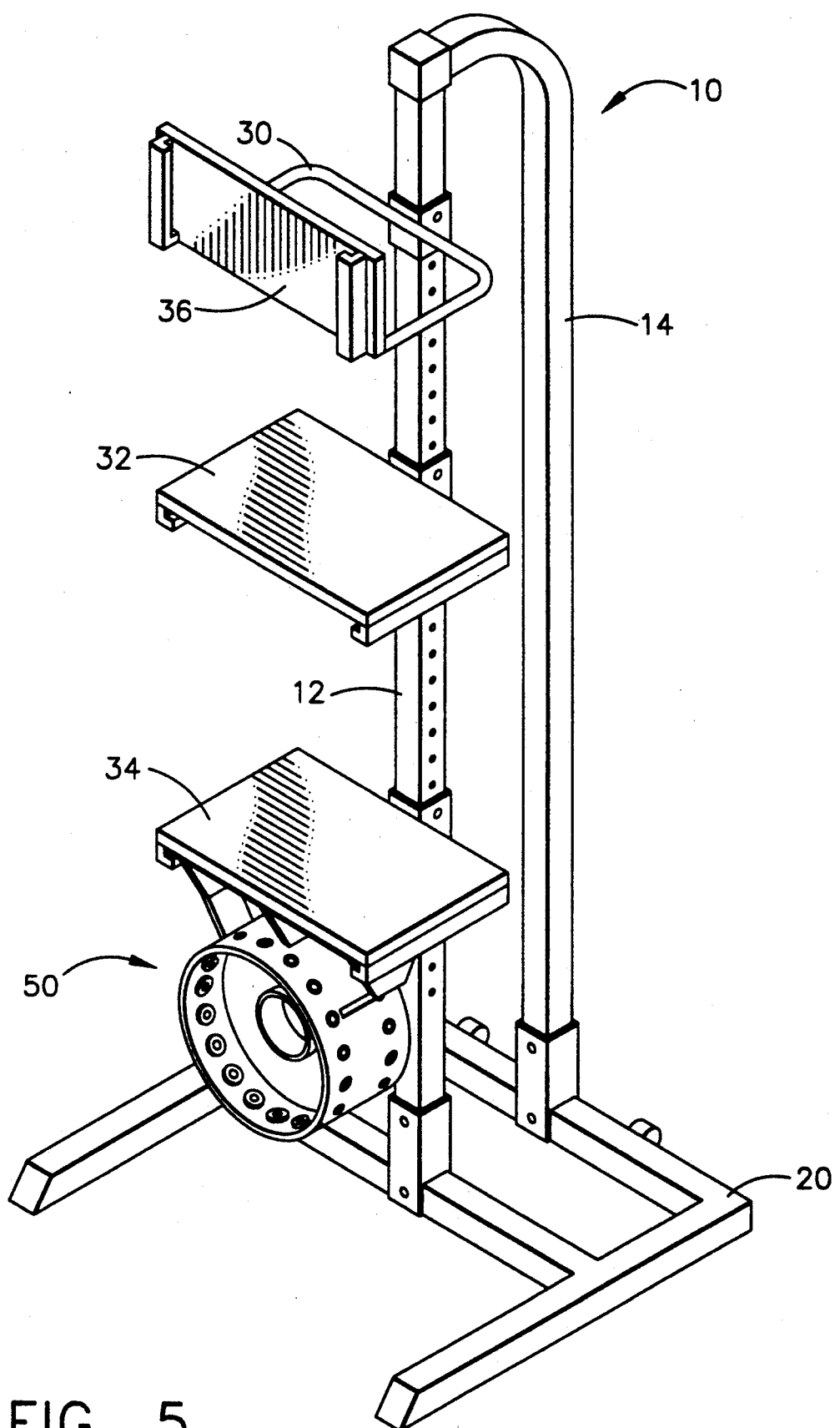
FIG. 5 is a perspective view of the portable testing apparatus of FIG. 2 with the dexterity testing apparatus attached at a knee level position.

The dexterity testing apparatus 50 can be mounted in any one of three mounting locations, which are shown in FIGS. 3, 4, and 5, by sliding the protrusions 82 of mounting plate 70 into the mounting bracket pairs 33a and 33b, 37a and 37b, or 35a and 35b, respectively. In FIG. 3, dexterity testing apparatus 50 is depicted as mounted along the bottom of the upper shelf 32. This is for use in the "elbow height" position. FIG. 4 depicts dexterity testing apparatus 50 in the "overhead" position, mounted to the overhead mounting plate 36. FIG. 5 depicts dexterity testing apparatus 50 attached to the lower shelf 34, for use in the "knee level" position.

Figure 9:
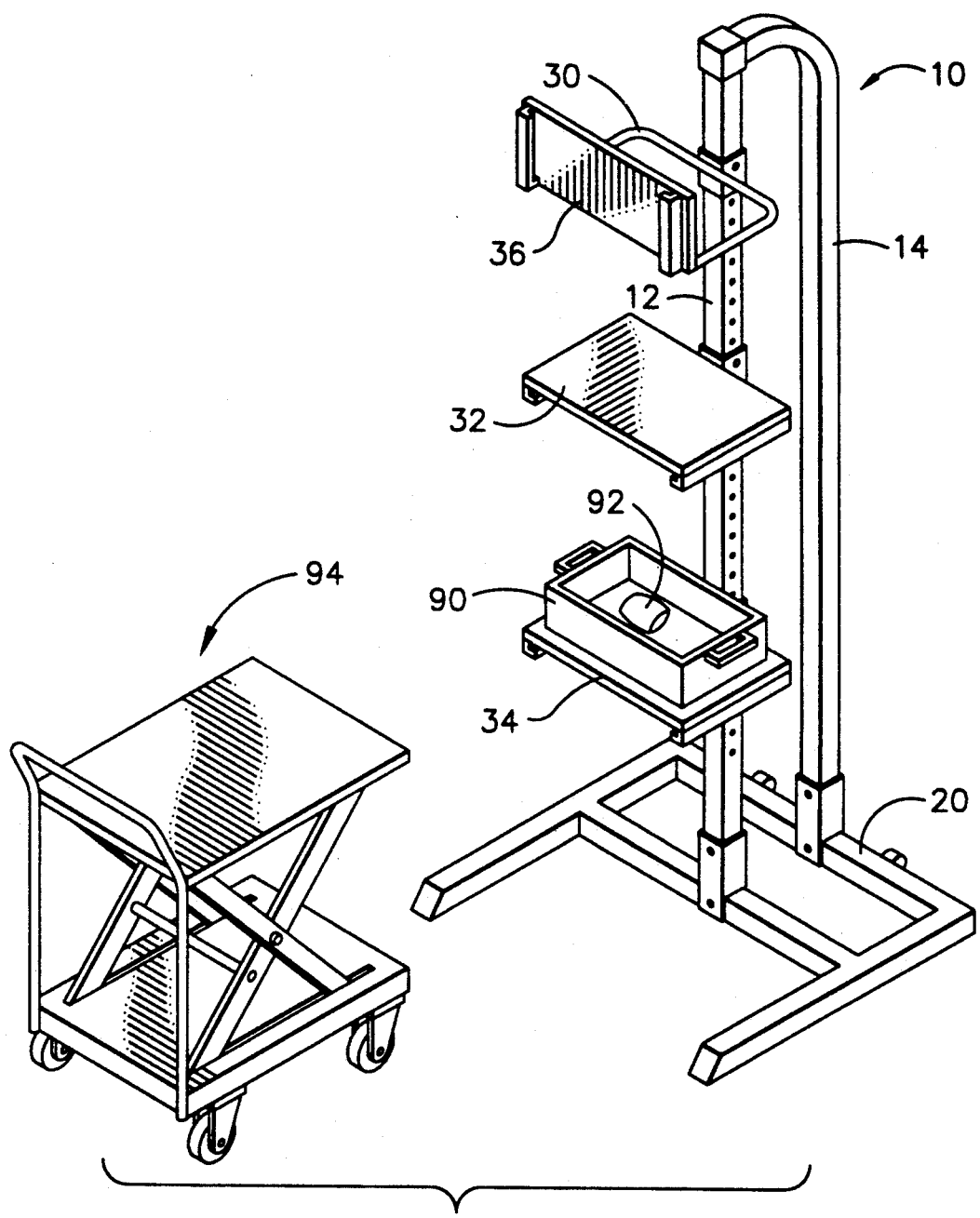
FIG. 9 is a perspective view of the portable testing apparatus of FIG. 2 with a tote pan on the bottom, knee level shelf, and a hydraulic cart.

FIG. 9 depicts the testing apparatus 10 for use with an industrial tote pan 90, which has handles on its sides. In the illustrated embodiment, industrial tote pan 90 is made of heavy-duty fiberglass.

Bags of leadshot 92 of known weight are placed into industrial tote pan 90 for use with the lifting ability testing of the human subject. An optional hydraulic cart 94 can be provided to assist in testing a person's lifting ability who is experiencing lower back pain while undergoing the lifting ability test. Hydraulic cart 94 is adjustable in height, so that an industrial tote pan 90 which is carrying bags 92 can be placed upon the top surface of the cart 94 at a height wherein the person being tested can comfortably bend and pick up the tote pan 90, while positioning his back in an erect position.

The testing apparatus described above is used to measure a person's ability to perform manual tasks at various work heights. The testing examiner would begin the evaluation by adjusting the position of the two shelves 32 and 34 in order to correspond to the test subject's proper heights for carrying and lifting the industrial tote pan 90, and by adjusting the position of the overhead horizontal mounting bracket 30 to the proper position above the test subject's head height. The correct heights are adjusted as follows: for the upper shelf 32, the tote pan 90 is placed upon the top of shelf 32, at which time the entire shelf/tote pan assembly is adjusted vertically until the tote pan's handle is at or just below shoulder height of the test subject. Such a vertical adjustment is performed by use of the upper shelf locator pin assembly 42, which is used to select the proper position hole 18 (the first available hole 18 that is at or below shoulder height) in the front vertical support 12, in order to achieve the correct height of upper shelf 32. To adjust the bottom shelf 34, the test subject holds the industrial tote pan 90 with his arms extended downward. The bottom shelf 34 is then adjusted to be at or just below the bottom of the tote pan 90 (at the first available position hole 18). To adjust the position of the overhead horizontal mounting bracket 30, the test subject stands erect in front of the testing apparatus 10, and the mounting bracket 30 is adjusted so that it is just above the clearance height of the test subject's head (at the first available position hole 18).

The first manual dexterity test is performed at elbow height, wherein the manual dexterity testing apparatus 50 is slid into the tracks mounted under the upper shelf 32 to begin the first activity. This work height minimizes the stress on the lower back and lower extremities, and also the shoulders. The test subject must use his hands and wrists throughout the normal range of wrist motions, including flexion, extension, pronation, and supination. Before the test is started, the testing examiner would demonstrate the dexterity activity to the test subject by transferring the bolts from the front to the back of the dexterity testing apparatus 50, while giving instructions verbally. An example of the dexterity test instructions follows:

Instructor: This is a test to see how well you can work with your arms, hands and fingers at various work heights. You should work as quickly and accurately as possible. The idea of this test is to transfer all eighteen nuts and bolts from the near side of the plastic cylinder to the same position on the far side. Do you prefer to use your right or left hand for writing or other activities?

Note: The examiner will point to the holes on near side and the far side. At this point, the examiner now begin to physically demonstrate the test while repeating the instructions below.

Instructor: You will begin the test by removing the first nut with your preferred hand. Grasp the head of the bolt firmly with your other hand while spinning the nut off the bolt with your preferred hand. Then transfer the nut through the central pipe fixture with your preferred hand, while at the same time placing the bolt through the hole on the far side with your other hand. You must screw the nut onto the bolt until the nut rests snugly against the plastic cylinder. You will transfer the first nine bolts in this manner, and then switch hands and spin the nuts off the remaining bolts with your opposite hand, while holding the heads of remaining nine bolts firmly with your preferred hand.

Note: The examiner will point to the tenth bolt and nut where the switch in hands occurs.

Instructor: Notice that the washers for the last nine bolts and nuts are a different color. This will help you remember to switch hands before transferring the remaining nine nuts and bolts. Continue working in a circular direction until all of the nuts and bolts have been transferred to the far side of the plastic cylinder. I would like you to finish transferring the remaining bolts for practice before we begin the timed test.

Note: Once all the bolts are transferred, the examiner turns the box 180 degrees in preparation for the timed test.

Instructor: When you complete the activity, I will ask you to assess your level of physical exertion during the activity. I will then ask you to assess your discomfort during the activity by having you rate your highest level of discomfort for each body part.

Note: The examiner will point to the exertion and discomfort sections on the wall chart, while repeating the following instructions.

Instructor: Do you have any questions? All right—go ahead. Work as quickly and accurately as possible. Tell me when you have finished.

Note: The stopwatch is started as soon as the examinee touches the first nut.

During this activity, the testing examiner uses a stop watch to time the test subject while performing the above test. This time is entered onto a physical ability database form (not shown).

Once a test subject has completed the elbow height activity, the testing examiner removes the dexterity testing apparatus 50 from the upper shelf and slides it into tracks mounted to the front of the overhead mounting plate 36. The test subject is allowed to rest for at least two minutes before starting the next activity. This overhead position does not require the test subject to raise on his toes in an unstable position, but does require the subject to raise both arms above the shoulders in a flexed position. The test subject's neck is extended (looking up), and his back is also extended. This position also places a sustained static load on the muscles of the neck and shoulders. The test subject must perform the identical test as to disassembling and reassembling the nuts and bolts 64 and 60. This test is also timed, and its working time period is recorded on the physical ability database form (not shown).

Once the test subject has completed the overhead dexterity activity, the testing examiner removes the dexterity testing apparatus 50 from overhead mounting plate 36 and slides it into the tracks mounted to the under surface of the lower shelf 34. Again, the test subject is allowed at least two minutes of rest between activities. At this position, the test subject's neck is flexed (looking down), his back is also flexed (bent), his shoulders are normal (at their sides), and his knees are flexed (either kneeling or bending). This working height places a sustained static load on the muscles of the back and lower extremities. At this point the test subject again undergoes the same disassembly and reassembly of the nuts and bolts 64 and 60. His working time is placed on the physical ability database form (not shown).

The above dexterity test procedure can also be used for a person who is sitting, for example, in a wheelchair. In such a case, the person is positioned just in front of the testing apparatus 10, and the dexterity testing apparatus 50 is mounted in the mounting brackets 35a and 35b of lower shelf 34, after lower shelf 34 is adjusted to the correct working height. The testing apparatus 10 has cross channels 21a and 21b which are separated by a sufficient distance to permit access for a standard wheelchair. The test subject is given the same instructions for disassembly, transfer, and reassembly of the nuts and bolts 64 and 60 as given to a normal person, as described above. After this activity is completed, the test subject can also be tested at the overhead position, by adjusting the overhead mounting bracket 30 to a position wherein the person can reach the dexterity testing apparatus 50 from his wheelchair. The test subject is again given the same instructions for disassembly, transfer, and reassembly of the nuts and bolts 64 and 60 as given to a normal person, as described above.

Now that the dexterity test has been completed, the test subject can perform the lifting ability test. The lifting ability test can independently test upper or lower body lifting. The normal procedure for this test is for the test subject to pick up the industrial tote pan 90, including a known weight of bags 92, from the floor to a carrying height, pivot, walk to the test apparatus 10, place the tote pan 90 onto the lower shelf 34, then lift the tote pan 90 from lower shelf 34 and further lift the tote pan 90 to shoulder height and place it onto the upper shelf 32. In this way, both lower body lifting and upper body lifting is tested. Most persons are stronger in their lower body than in their upper body, so that they will reach their weight limit in attempting to lift the weight up to the shoulder level and place it onto upper shelf 32. Once that has occurred, the lower body lifting test can continue, wherein the test subject picks up the tote pan 90 with the bags 92 from the floor, raises to carrying height, pivots, walks over to the test apparatus 10 and places the tote pan 90 onto the lower shelf 34. The carrying height is the position of the tote pan 90 when the test subject holds tote pan 90 in front of himself, with his arms relatively straightened and extended down. The maximum weights that the test subject can comfortably handle are recorded on the physical ability database form (not shown) for both the upper body lifting ability, and for the lower body lifting ability.

Before the test is started, the testing examiner would review the test subject's responses to the dexterity test. If the test subject did not experience significant discomfort during the prior dexterity activity, then the testing examiner would give verbal instructions as to the lifting ability activity. An example of the such test instructions follows:

Instructor: This is a test to see how much weight you can lift smoothly, without overstraining, at various work heights. Do not strain or hurry your lift. I will stop or correct you immediately if I observe you having any difficulty in making a smooth, coordinated lift.

Note: At this point, the examiner physically demonstrates the lifting test while repeating the instructions below.

Instructor: We would like you to lift the pan from the floor, pivot, and carry the pan to the lower shelf. You may pause as long as you would like between each lift. Then we would like you to lift the pan to the upper shelf, by stepping back and lifting the box while keeping your elbows raised. Then you will return the pan to its starting position on the floor, by stepping back, lowering the pan to your waist, pivoting, and lowering the pan to its initial starting position. At this point, you will be asked whether you would like to add additional weight to the pan and continue. You will be also be asked to report your level of physical exertion and discomfort during the lifting cycle. Do you have any questions? Go ahead and complete one lifting cycle.

Note: At this point, the examiner observes the examinee complete one lifting cycle with an empty tote pan. During this process, the examiner instructs the client in proper lifting mechanics.

Instructor: After we have determined the maximum amount of weight you can lift smoothly, without overstraining for either the lower or upper lift, the testing may be continued for the other lifting condition. Remember, we are interested in determining how much weight you are able to handle safely, without hurrying or overstraining. This is your chance to help us set safe lifting limits.

If the test subject tires from the upper body lifting, he does not have to continue the upper body lifting procedure, but can further proceed with the lower body lifting procedure as follows: the test subject picks up the tote pan 90 from the floor, pivots, then walks to the test apparatus 10 and places tote pan 90 onto the lower shelf 44. If the person tires from the lower body lifting, he does not have to continue the lower body lifting procedure, but can further proceed with the upper body lifting procedure as follows: the test subject picks up the tote pan 90 from the lower shelf 44, steps back one pace, lifts the weight to shoulder height, and steps forward while placing the tote pan 90 onto the upper shelf 32.

If the test subject experienced significant back or lower extremity discomfort during the prior dexterity testing activity, the testing examiner can use the hydraulic cart 94 to test lifting ability from a height the person can bend his knees or back comfortably, rather than lifting tote pan 90 from the floor height. In this way, the person's lower body lifting strength can still be cautiously evaluated without injuring his back or lower extremities, or, under extreme circumstances, not evaluated at all. On the other hand, if the test subject experienced significant upper extremity discomfort which prevented him from performing the upper body lifting tests, then his upper body lifting strength evaluation may have to be canceled.

A person's continuous maximum lifting strength can also be determined using the industrial tote pan 90, bags 92, and the testing apparatus 10 of the present invention. Rather than adding weight to the tote pan 90 until the test subject cannot further lift tote pan 90 even one more time, the weight in tote pan 90 can be gradually increased while the test subject lifts tote pan 90 a repeated number of times at a fixed weight within a relatively short time span, much like performing repetitions while weight-lifting. After a short rest period, the test subject performs the same repetitive lifting test at a greater weight until he cannot repeatedly lift that weight. This repetitive test is performed for both upper-body lifting and lower-body lifting, as described above, and can, therefore, be used to independently discover the test subject's lifting ability in both categories.

A report of the test subject's physical ability can be generated from the data that was previously recorded on the physical ability database form (not shown). Such a report can also include physical aptitudes which are measured by other standardized tests, such physical aptitudes as balance and agility, eye/hand coordination, color discrimination, vision, and hearing acuity. The conclusion of the report would normally be a recommendation as to what type of work the test subject is qualified to perform, based upon the objective criteria of the testing method of the present invention.

In summary, numerous benefits have been described which result from employing the concepts of the invention. The method of testing dexterity requires a full range of wrist motion at each of three different height-—elbow height, overhead height, and below waist height. Vision is not obscured during these dexterity tests, due to the clear plastic used in the dexterity testing apparatus, which places women on a more-equal footing with men so that women can produce test scores that are nearly equal to those of men. The method allows for independent evaluations at each height because each height is a static test. The person works at a given height for the entire testing interval, and does not constantly change heights as in tests known in the prior art. Independent evaluations at each height are also given for the lifting ability test, which can be modified for persons experiencing lower back pain. The method of testing in accordance with the present invention allows for a streamlined test procedure, which can be performed on many test subjects rather quickly.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

I claim:

1. A method for testing and evaluating the dexterity and range of motion of substantially the entire musculoskeletal system of a human test subject, comprising the steps of:

(a) directing the subject's hand and wrist into a dexterity tester positioned at a first predetermined height and placing the subject into a first posture;

(b) requiring the subject while in the first posture to manipulate a plurality of mechanical parts in the dexterity tester in a predetermined manner that requires the subject's hand and wrist to undergo a complete range of motion while the wrist is in an awkward position, said awkward position being achieved by confining the wrist within an opening of said dexterity tester while forcing the hand past an obstacle portion of said dexterity tester proximal to its opening before reaching said plurality of mechanical parts;

(c) measuring the time required for the subject while in the first posture to so manipulate the parts at the first predetermined height;

(d) thereafter directing the subject's hand and wrist into a dexterity tester positioned at a second predetermined height which is different from said first predetermined height and placing the subject into a second posture which is different from said first posture;

(e) requiring the subject while in the second posture to manipulate a plurality of mechanical parts in the dexterity tester in a predetermined manner that requires the subject's hand and wrist to undergo a complete range of motion while the wrist is in an awkward position, said awkward position being achieved by confining the wrist within an opening of said dexterity tester while forcing the hand past an obstacle portion of said dexterity tester proximal to its opening before reaching said plurality of mechanical parts;

(f) measuring the time required for the subject while in the second posture to so manipulate the parts at the second predetermined height independently of the time required for manipulation at the first height;

(g) thereafter directing the subject's hand and wrist into a dexterity tester positioned at a third predetermined height which is different from both said first and second predetermined heights and placing the subject into a third posture which is different from both said first and second postures;

(h) requiring the subject while in the third posture to manipulate a plurality of mechanical parts in the dexterity tester in a predetermined manner that requires the subject's hand and wrist to undergo a complete range of motion while the wrist is in an awkward position, said awkward position being achieved by confining the wrist within an opening of said dexterity tester while forcing the hand past an obstacle portion of said dexterity tester proximal to its opening before reaching said plurality of mechanical parts; and (i) measuring the time required for the subject while in the third posture to so manipulate the parts at the third predetermined height independently of the time required for manipulations at the first and second heights.

2. A method as recited in claim 1, wherein said first predetermined height is at elbow height, said second predetermined height is at overhead height, and said third predetermined height is at below waist height.

3. A method as recited in claim 1, wherein said step to manipulate a plurality of mechanical parts in the dexterity tester in a predetermined manner includes the disassembly and reassembly of a plurality of nuts and bolts.

4. A method as recited in claim 1, wherein the testing is conducted with a physical abilities tester that includes first and second shelves and a mounting bracket which are adjustable in height, said first and second shelves and mounting bracket being capable of supporting said dexterity tester, said first and second shelves additionally being capable of supporting an industrial tote pan, further comprising the steps of:

(a) adjusting, before the test begins, the height of said first shelf of said physical abilities tester to a height which is at or just below the bottom surface of said industrial tote pan while said industrial tote pan is being held by the human test subject whose hands are positioned at shoulder height;

(b) adjusting, before the test begins, the height of said second shelf of said physical abilities tester to a height which is at or just below the bottom surface of said industrial tote pan while said industrial tote pan is being held by the human test subject whose arms are extended downward; and (c) adjusting, before the test begins, the height of said horizontal mounting bracket of said physical abilities tester to a height which is above the top-most portion of the human test subject's head while the human test subject is standing erect.

5. A method for testing and evaluating dexterity of a human test subject who is sitting, comprising the steps of:

(a) directing the subject's hand and wrist into a transparent dexterity tester positioned at a predetermined height;

(b) requiring the subject to manipulate a plurality of mechanical parts in the dexterity tester in a predetermined manner that requires the subject's hand and wrist to undergo a complete range of motion while the wrist is in an awkward position, said awkward position being achieved by confining the wrist within an opening of said dexterity tester while forcing the hand past an obstacle portion of said dexterity tester proximal to its opening before reaching said plurality of mechanical parts; and (c) measuring the time required for the subject to so manipulate the parts at the predetermined height.

6. A method as recited in claim 5, wherein said predetermined height is at elbow height.

7. A method as recited in claim 5, wherein said predetermined height is at overhead height.

* * * * *